(12) United States Patent
Boissonneault

(10) Patent No.: US 7,935,691 B2
(45) Date of Patent: May 3, 2011

(54) EXTENDED CYCLE MULTIPHASIC ORAL CONTRACEPTIVE KIT

(75) Inventor: Roger M. Boissonneault, Long Valley, NJ (US)

(73) Assignee: Warner Chilcott Company, LLC, Fajardo, PR (US)

( * ) Notice: Subject to any disclaimer, the term of this patent is extended or adjusted under 35 U.S.C. 154(b) by 0 days.

(21) Appl. No.: 12/534,902

(22) Filed: Aug. 4, 2009

(65) Prior Publication Data

US 2009/0291927 A1 Nov. 26, 2009

Related U.S. Application Data

(62) Division of application No. 11/078,300, filed on Mar. 14, 2005, now Pat. No. 7,569,560.

(60) Provisional application No. 60/554,621, filed on Mar. 19, 2004.

(51) Int. Cl.
*A61K 31/56* (2006.01)

(52) U.S. Cl. ...................................................... 514/170

(58) Field of Classification Search ................... 514/170
See application file for complete search history.

(56) References Cited

U.S. PATENT DOCUMENTS

| | | | |
|---|---|---|---|
| 4,390,531 A | 6/1983 | Edgren | 424/239 |
| 4,621,079 A | 11/1986 | Lachnit-Fixson et al. | 514/170 |
| 4,921,843 A | 5/1990 | Pasquale | 514/170 |
| 4,962,098 A | 10/1990 | Boissonneault | 514/170 |
| 5,010,070 A | 4/1991 | Boissonneault | 514/171 |
| 5,888,543 A | 3/1999 | Gast | 424/464 |
| 5,898,032 A | 4/1999 | Hodgen | 514/178 |
| 2003/0139381 A1 | 7/2003 | Bell et al. | 514/170 |
| 2004/0220152 A1 | 11/2004 | Ben-Maimon et al. | 514/170 |

FOREIGN PATENT DOCUMENTS

WO WO98/04268 5/1998

OTHER PUBLICATIONS

Edwards, L.A. "An Update on Oral Contraceptive Options", Formulary 2004 United States, vol. 39, No. 2, Feb. 2004 pp. 104-121.
Hamerlynck J.V. Th et al. "Postponement of Withdrawal Bleeding in Women Using Low-Dose Combined Oral Contraceptives" Contraception, Geron-X, Inc., Los Altos, Ca, US, vol. 35, No. 3, 1987 pp. 199-206.

*Primary Examiner* — Barbara P Badio
(74) *Attorney, Agent, or Firm* — Fitzpatrick, Cella, Harper & Scinto

(57) ABSTRACT

A multiphasic contraceptive kit for use to practice a multiphasic method of contraception that provides for sequentially administering to a female of child bearing age: (a) a Phase I composition containing a progestogen and an estrogen for about 4 to about 7 days; (b) a Phase II composition containing a progestogen and an estrogen for about 8 to about 16 days; (c) a Phase III composition containing a progestogen and an estrogen for about 4 to about 7 days; and (d) optionally, a Phase IV composition which is a placebo or a non-steroidal component, wherein the ethinyl estradiol equivalent amount of estrogen in the Phase II composition is at least 5 mcg greater than the ethinyl estradiol equivalent amount of estrogen in each of the Phase I and III compositions. Preferably the sequential administration is repeated the day following the completion of the administration of the Phase III compositions providing an extended cycle multiphasic oral contraceptive method.

21 Claims, No Drawings

EXTENDED CYCLE MULTIPHASIC ORAL CONTRACEPTIVE KIT

RELATED CASES

This application is a divisional of application Ser. No. 11/078,300, filed Mar. 14, 2005, now U.S. Pat. No. 7,569,560, claims benefit of that application under 35 U.S.C. §120, which claims benefit under 35 U.S.C. §119 of 60/554,621, filed on Mar. 19, 2004, and incorporates the entire contents of both of those prior applications by reference.

BACKGROUND OF THE INVENTION

1. Field of the Invention

This invention is directed to a multiphasic estrogenic/progestogenic contraceptive regimen that may be used for an extended period of time. In the multiphasic regimen of the present invention, the amount of estrogen administered in an intermediate phase is greater than the amount of estrogen administered in the first and final phases. The inventive regimen provides contraceptive efficacy and enables the user to maintain menstrual cycle control. A multiphase contraceptive kit that may be used to practice the method of this invention is also contemplated.

2. Related Background Art

Contraceptive compositions containing both estrogenic and progestogenic compounds are known to be highly effective in controlling ovulation and conception. The progestogenic component of the composition is primarily responsible for the contraceptive efficacy of the composition, while the estrogenic component is included to reduce undesired side effects, such as breakthrough bleeding or spotting. In fact, small amounts of estrogen help stabilize the endometrium and allow cyclic withdrawal bleeding, similar to the natural menstrual cycle.

The earliest of these estrogenic/progestogenic contraceptive compositions was administered monophasically (fixed dose) and contained a relatively high level of estrogenic component. To minimize estrogen's major negative side effect on blood clotting factors, the dose of estrogen was reduced over time. However, as estrogen doses decreased, the incidences of unwanted breakthrough bleeding or spotting have generally increased.

Multiphasic oral contraceptives were introduced to artificially simulate the natural rise of progesterone over the cycle in an attempt to solve this problem. A constant goal, however, has been to reduce the estrogenic potency of such compositions without reducing contraceptive efficacy and increasing undesired side effects.

In U.S. Pat. No. 5,888,543, various regimens are disclosed where a combination of progestin and estrogen are administered in a monophasic or multiphasic regimens (varied dose, e.g., biphasic or triphasic). In one embodiment, a combination of a progestin composition and an estrogen composition is administered such that the daily dosage of the second phase progestin is greater than the daily dosage of progestin in the first phase and the daily dosage of the second phase estrogen is greater than or equal to the daily dosage of estrogen in the first phase.

A particularly advantageous technique for reducing total estrogenic administration is described in U.S. Pat. No. 4,962,098. This describes a triphasic method of contraception using a progestogen/estrogen combination in which the amount of estrogen is increased stepwise over the three phases. The first phase is 4-7 days, the second phase is 5-8 days and the third phase is 7-12 days. Preferably, the administration of the contraceptive compositions for the three phases will be 21 days followed by a 7 day placebo period. For all three phases the progestogen is 0.5 to 1.5 mg of norethindrone acetate, while about 10 to 30 mcg of ethinyl estradiol is used in the first phase, about 20 to 40 mcg of ethinyl estradiol is used in the second phase and 30 to 50 mcg of ethinyl estradiol is employed in the third phase.

U.S. Pat. No. 5,010,070 is related to U.S. Pat. No. 4,962,098 and discloses a multiphasic contraceptive kit containing ethinyl estradiol and norethindrone acetate in first, second, and third phase compositions.

An extended oral contraceptive regimen is disclosed in U.S. Pat. No. 5,898,032, where estrogen and progestin are administered in a combined dosage form, preferably monophasicly, for 60 to 110 consecutive days, followed by an administration free period of 3 to 10 days. The amount of estrogen and progestin administered daily are equivalent to about 5-35 mcg of ethinyl estradiol and about 0.025 to 10 mg of norethindrone acetate, respectively. In one particular embodiment, the combined dosage form is administered for 84 days followed by 7 pill free days. Following this particular regimen is said to result in four treatments and menstrual cycles during the year.

There are, however, disadvantages to using an extended monophasic oral contraceptive regimen. Typically, monophasic oral contraceptives administered for an extended period of time have poor initial cycle control. Another disadvantage is that once breakthrough bleeding is under control, the user becomes functionally amenorrheic. Psychologically, this does not reassure the user that she is not pregnant.

An extended cycle regimen that employs a multiphasic contraceptive method has not been described or suggested. A major concern is that multiphasic methods vary the ratio of estrogen to progestogen such that the amount of estrogen and/or progestogen administered in the final phase, e.g., Phase III, is much greater than the amount of estrogen and/or progestogen administered in the initial phase, e.g., Phase I. In an extended cycle regimen, where the cycle proceeds sequentially from the first phase through the final phase and repeats again starting with the first phase, the dramatic decrease in estrogen and/or progestogen from the final phase to the first phase would increase the potential for breakthrough bleeding, which is unacceptable.

An extended oral contraceptive regimen that reduces the risk that the user becomes functionally amenorrheic while taking advantage of the benefits of a multiphasic contraceptive method, e.g., reduce risk of breakthrough bleeding, improved control of bleeding, and effective means of contraception, would be highly desirable to users.

SUMMARY OF THE INVENTION

The present invention is directed to a multiphasic method of contraception that provides for sequentially administering to a female of child bearing age (a) a Phase I composition containing a progestogen in an amount equivalent to about 0.5 to about 1.5 mg norethindrone acetate and an estrogen in an amount equivalent to about 5 to about 30 mcg of ethinyl estradiol for about 4 to about 7 days; (b) a Phase II composition containing a progestogen in an amount equivalent to about 0.5 to about 1.5 mg of norethindrone acetate and an estrogen in an amount equivalent to about 10 to about 40 mcg of ethinyl estradiol for about 8 to about 16 days; (c) a Phase III composition containing a progestogen in an amount equivalent to about 0.5 to about 1.5 mg of norethindrone acetate and an estrogen in an amount equivalent to about 5 to about 30 mcg of ethinyl estradiol for about 4 to about 7 days; and (d)

optionally, a Phase IV composition which is a placebo or a non-steroidal component, such as for example, ferrous fumarate, for about 2 to about 9 days, wherein the ethinyl estradiol equivalent amount of estrogen in the Phase II composition is at least 5 mcg greater than the ethinyl estradiol equivalent amount of estrogen in each of the Phase I and III compositions.

In a particularly significant embodiment of the invention, the sequential administration of the Phase I, II, and III compositions is repeated the day following the completion of the administration of the Phase III composition to provide an extended cycle multiphasic oral contraceptive method. Preferably, the extended contraceptive cycle is in a range from about 42 to about 140 days, and, preferably, about 63 to about 120 days.

Yet another embodiment of this invention is directed to a multiphase combination and contraceptive kit comprising a package containing daily dosages of (a) a Phase I composition containing a progestogen in an amount equivalent to about 0.5 to about 1.5 mg of norethindrone acetate and an estrogen in an amount equivalent to about 5 to about 30 mcg of ethinyl estradiol; (b) a Phase II composition containing a progestogen in an amount equivalent to about 0.5 to about 1.5 mg of norethindrone acetate and an estrogen in an amount equivalent to about 10 to about 40 mcg of ethinyl estradiol; (c) a Phase III composition containing a progestogen in an amount equivalent to about 0.5 to about 1.5 mg of norethindrone acetate and an estrogen in an amount equivalent to about 5 to about 30 mcg of ethinyl estradiol; and (d) optionally, a Phase IV composition which is a placebo or a non-steroidal component, wherein the ethinyl estradiol equivalent amount of estrogen in the Phase II composition is at least 5 mcg greater than the ethinyl estradiol equivalent amount of estrogen in each of the Phase I and III compositions.

The kit may be designed for single cycle or extended cycle use. For single cycle use the kit contains about 4 to about 7 dosages of the Phase I composition; about 8 to about 16 dosages of the Phase II composition; and about 4 to about 7 dosages of the Phase III composition. For extended cycle use, the kit will preferably contain a plurality of groups of dosages of the Phase I, Phase II, and Phase III compositions. Both the single cycle and extended cycle kits, optionally and preferably, may contain about 2 to about 9 dosages of a Phase IV composition. Of course, it is also possible to practice the extended cycle of this invention by employing a plurality of the above-described kits for single cycle use.

DETAILED DESCRIPTION OF THE INVENTION

For the purposes of this invention, the designation "mcg" refers to micrograms and "mg" to milligrams.

By practicing the multiphasic contraceptive method disclosed herein, a user advantageously improves control of menstrual bleeding while taking the estrogenic/progestogenic contraceptive compositions of the invention.

A notable feature of the invention is that the amount of estrogen administered in the intermediate phase composition (Phase II) is greater than the amount of estrogen administered in each of the first and final phase compositions (Phase I and Phase III). Moreover, it is desirable to have the amount of estrogen administered in the first phase composition (Phase I) correspond to the amount of estrogen administered in the final phase composition (Phase III). In one particularly preferred embodiment the amount of ethinyl estradiol in the Phase II composition is at least about 5 mcg greater, preferably at least about 10 mcg greater, than the amount of ethinyl estradiol in each of the Phase I and Phase III compositions.

In one particularly preferred embodiment the amount of estrogen in Phase I is equivalent to about 20 mcg of ethinyl estradiol, the amount of estrogen in Phase II is equivalent to about 25 mcg of ethinyl estradiol and the amount of estrogen in the Phase III is equivalent to about 20 mcg of ethinyl estradiol. In yet another particularly preferred embodiment the amount of estrogen in Phase I is equivalent to about 25 mcg of ethinyl estradiol, the amount of estrogen in Phase II is equivalent to about 30 mcg of ethinyl estradiol and the amount of estrogen in Phase III is equivalent to about 25 mcg of ethinyl estradiol.

The progestogen may be selected, for example, from the group consisting of norethindrone acetate, drospirenone, trimegestone, norethindrone, levonorgestrel, desogestrel, 3-ketodesogestrel, gestodene and the like. The most preferred progestogen is norethindrone acetate. The estrogen may be selected, for example, from the group consisting of ethinyl estradiol, 17-β-estradiol, estradiol acetate, conjugated estrogens, mestranol, estrone and salts thereof. The most preferred estrogen is ethinyl estradiol. The amount of progestogen and estrogen employed in each Phase will be that amount which is equivalent in potency to the ranges of norethindrone acetate and ethinyl estradiol, respectively, that are set forth herein. Determination of equivalent potency is well understood and readily accomplished by those of ordinary skill in the art.

In the female body, the blood-rich mucous membrane lining the uterus known as the endometrium, adapts to varying levels of estrogen in the body. Without wishing to be bound by theory, it is believed that by cycling low amounts of estrogen (e.g., decreasing the amount of estrogen in the final phase of administration to levels corresponding to the initial phase), the integrity of the endometrium may be maintained at an adequate state of at least about 3 to 5 mm thickness, thus reducing the undesirable occurrence of breakthrough bleeding. By maintaining the integrity of the endometrium, the user may control discharge bleeding and extend her cycle. By varying the dose of estrogens the endometrium does not acclimate to a constant estrogenic dose. It is believed, without being bound by theory, that this up and down regulation of the estrogenic endometrium receptors results in the support of the endometrium.

The inventive multiphasic method of contraception sequentially administers, to a female of child bearing age: (a) a Phase I composition comprising a progestogen in an amount equivalent to about 0.5 to about 1.5 mg norethindrone acetate and an estrogen in an amount equivalent to about 5 to about 30 mcg ethinyl estradiol; (b) a Phase II composition comprising a progestogen in an amount equivalent to about 0.5 to about 1.5 mg norethindrone acetate and an estrogen in an amount equivalent to about 10 to about 40 mcg ethinyl estradiol; (c) a Phase III composition comprising a progestogen in an amount equivalent to about 0.5 to about 1.5 mg norethindrone acetate and an estrogen in an amount equivalent to about 5 to about 30 mcg ethinyl estradiol; and (d) optionally, a Phase IV composition which is a placebo or a non-steroidal component. Moreover, the ethinyl estradiol equivalent amount of estrogen administered in the Phase II composition is at least about 5 mcg greater, preferably at least about 10 mcg greater, than the ethinyl estradiol equivalent amount of estrogen administered in each of Phases I and III.

In a preferred embodiment, the regimen is practiced in an extended cycle manner. In the first cycle, Phase I is administered for about 4 to about 7 days, Phase II is administered for about 8 to about 16 days, and Phase III is administered for about 4 to about 7 days. It is essential that the phases succeed each other in increasing order (i.e., I, II, and III). Upon completion of Phase III, the user immediately repeats the cycle by starting Phase I again. Preferably, this may be repeated for a period of about 42 days to about 140 days, more preferably, about 63 to about 120 days. When the user desires to discontinue the regimen, and experience a discharge bleeding, she will either begin administering the Phase IV composition or go pill free for a period of about 2 to about 9 days, preferably about 4 to about 9 days. By practicing this regimen, the user may reduce the number of menstrual cycles she will have to as little as three per year.

In another embodiment, the user may choose to psychologically reassure herself that she is not pregnant by having a monthly discharge bleeding. To do so, she would practice the inventive regimen in a single cycle manner and upon completion of Phase III, either begin taking a Phase IV composition or simply take no pill for about 2 to about 9 days. For example, in a preferred embodiment of the single cycle method the user would follow the regimen where Phase I is administered for about 4 to about 7 days, Phase II is administered for about 8 to about 16 days, Phase III is administered for about 4 to about 7 days, and Phase IV is administered for about 2 to about 9 days. Ideally, this embodiment of the inventive method is practiced for a 28 day period (menstrual cycle). It is essential that the phases succeed each other in increasing order (i.e., I, II, III, IV). After the Phase IV composition is administered, the user may start the cycle again beginning with the Phase I composition.

The Phase IV composition may serve as a cleansing period. In Phase IV, a placebo or a non-steroidal component may be administered.

In a particularly preferred embodiment, the Phase IV composition is a non-steroidal component comprising an iron supplement. Suitable iron supplements include, for example, ferrous fumarate, ferrous sulfate, ferrous gluconate, iron polysaccharides, and mixtures thereof. The preferred iron supplement is ferrous fumarate.

Preferably, the iron supplement is equivalent to not more than about 75 mg ferrous fumarate.

The compositions used herein preferably contain norethindrone acetate, a progestogenic component having less potency—and, comcomitantly, producing lower incidence of breakthrough bleeding—than other progestogenic agents, e.g., norethindrone.

As noted previously, it is essential that the method of this invention be practiced by administration of the compositions in a numeric sequence with the Phase I composition administered first, the Phase II composition administered second, etc. If packaging and/or other requirements dictate, the method and kit described herein can be employed as part of a larger scheme for contraception or treatment of gynecological disorders. While the sequence in which Applicant's combinations are administered is important to their operation, it should be kept in mind that variations in timing and dosage can be tolerated when medical considerations so dictate.

Although ethinyl estradiol is the estrogenic compound exemplified in this invention, it should be understood that other estrogenic compounds may be substituted as long as the equivalent amount of estrogen is administered. Other suitable estrogenic compounds include, for example, 17β-estradiol, estradiol acetate conjugated estrogens, mestranol, estrone, and salts thereof. Preferred salts of estrone include, but are not limited to the sodium and piperate salt. For the conjugated estrogens, 1.25 mg conjugated estrogens is equivalent to a daily dose of 15 mcg ethinyl estradiol.

Similarly, norethindrone acetate is the progestogenic compound exemplified in this invention. However, other suitable progestogenic compounds may be substituted so long as the equivalent amount of progestogen is administered. Suitable progestogenic compounds include, but are not limited to, levonorgestrel, desogestrel, drospirenone, trimegestone, 3-ketodesogestrel, gestodene, and the like.

The compositions employed in accordance with the invention in Phases I through IV will more preferably have the administration times and drug contents set forth in the Tables 1 and 2, when a four-phase system is used. Each table sets forth relevant values for one of Applicant's preferred embodiments, or configurations, for administration of the system to females.

TABLE 1

| Phase | Days | mg Norethindrone acetate | mcg EE | mg Fumarate |
|---|---|---|---|---|
| I | 5 | 1.0 | 25 | 0 |
| II | 11 | 1.0 | 30 | 0 |
| III | 5 | 1.0 | 25 | 0 |
| IV | 7 | 0 | 0 | 75 |

TABLE 2

| Phase | Days | mg Norethindrone acetate | mcg EE | mg Fumarate |
|---|---|---|---|---|
| I | 5 | 1.0 | 20 | 0 |
| II | 14 | 1.0 | 25 | 0 |
| III | 5 | 1.0 | 20 | 0 |
| IV | 4 | 0 | — | 75 |

It should be noted that these tables are presented for illustrative purposes only. For example, the cycles described in Table 1 and Table 2 could be modified by dropping the Phase IV composition and sequentially administering Phase I, II, and III and then immediately repeating the administration of Phase I, II, and III for an extended cycle method of oral contraception. The substitution of functionally equivalent amounts and kinds of reagent(s) in these schemes is contemplated. For example, the use of sugar or other placebo in place of all or part of the ferrous fumarate is envisioned.

In addition, the use of other conventional additives, e.g., fillers, colorants, polymeric binders, and the like is also contemplated. In general any pharmaceutically-acceptable additive which does not interfere with the function of the active components can be used in one or more of the compositions.

Suitable carriers with which the compositions can be administered include lactose, starch, cellulose derivatives and the like used in suitable amounts. Lactose is a preferred carrier. Mixtures of carriers are operable.

The terms "method" and "kit" are used herein to encompass any drug delivery systems via the use of which the 3- or 4-phase scheme outlined above can be effectively administered to human females. Combinations of various dosage forms are operable.

The multiphase combination and contraceptive kit of this invention is a package containing the daily dosages of Phase I, II, and III compositions and optionally the daily dosages of Phase IV composition for practicing the method of this invention. Various types of packages for holding contraceptives are well known and it is contemplated that any such packaging may be used or altered for use in the practice of the present invention. For example, a single cycle package of the present invention would preferably include about 4 to about 7 dosages of the Phase I composition; about 8 to about 16 dosages of the Phase II composition; and about 4 to about 7 dosages of the Phase III composition. A preferred embodiment of the single cycle package may also include about 2 to about 9 dosages of the Phase IV composition. It should be readily apparent that groups of dosages or a plurality of single cycle packages could be used to practice the extended cycle multiphasic oral contraceptive method of this invention. The plurality of packages could be the same or different. For example, the user could have three or four packages that each contain the above-described dosages of Phase I, II, and III compositions. Preferably, the kit would include about 2 to about 9 groups, more preferably about 3 to about 5 groups, of dosages of the Phase I, II, and III compositions. In another embodiment, each group of dosages of the Phase I composition contains about 5 dosages, each group of dosages of the Phase II composition contains about 11 to about 14 dosages, and each group of dosages of the Phase III composition contains about 5 dosages. If desired, the last package to be used in the extended cycle administration could also contain the optional Phase IV composition that is taken prior to beginning the next extended cycle administration. Of course, a single package may contain all the dosages necessary for an extended cycle administration. In this case, there would be a plurality of groups of dosages of the Phase I, II, and III compositions, and optionally a last group of dosages of the Phase IV composition. In such a package the dosages would be taken sequentially and grouped such that each group of dosages would be administered in a cyclical fashion (e.g., I, II, III, I, II, III, I, II, III, I, II, III for a four cycle extended cycle followed optionally by IV).

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A multiphase combination and contraceptive kit comprising a package containing daily dosages of:
   (a) a Phase I composition containing a progestogen in an amount equivalent to about 0.5 to about 1.5 mg of norethindrone acetate and an estrogen in an amount equivalent to about 5 to about 30 mcg of ethinyl estradiol;
   (b) a Phase II composition containing a progestogen in an amount equivalent to about 0.5 to about 1.5 mg of norethindrone acetate and an estrogen in an amount equivalent to about 10 to about 40 mcg of ethinyl estradiol; and
   (c) a Phase III composition a progestogen in an amount equivalent to containing about 0.5 to about 1.5 mg of norethindrone acetate and an estrogen in an amount equivalent to about 5 to about 30 mcg of ethinyl estradiol;
   wherein the ethinyl estradiol equivalent amount of estrogen in the Phase II composition is at least 5 mcg greater than the ethinyl estradiol equivalent amount of estrogen in each of the Phase I and III compositions, wherein the ethinyl estradiol equivalent amount of estrogen in the Phase III composition is equal to the ethinyl estradiol equivalent amount of estrogen in the Phase I composition, and wherein the sequential administration of the Phase I, II, and III compositions is repeated the day following the completion of the administration of composition III to provide an extended contraceptive cycle, there is no decrease in the norethindrone acetate equivalent amount of progestogen from the administration of the Phase III composition to the administration of the Phase I composition in the extended contraceptive cycle and the extended contraceptive cycle is from about 42 to about 140 days.

2. The kit according to claim 1, wherein the progestogen is selected from the group consisting of norethindrone acetate, drospirenone, trimegestone, norethindrone, levonorgestrel, desogestrel, 3-ketodesogestrel, gestodene, and mixtures thereof.

3. The kit according to claim 2, wherein the progestogen is norethindrone acetate.

4. The kit according to claim 1, wherein the estrogen is selected from the group consisting of ethinyl estradiol, 17β-estradiol, estradiol acetate, conjugated estrogens, mestranol, estrone, and salts thereof.

5. The kit according to claim 4, wherein the estrogen is ethinyl estradiol.

6. The kit according to claim 1, wherein the kit further comprises about 2 to about 9 dosages of a Phase IV composition which is a placebo or a non-steroidal component to be administered upon completion of the extended contraceptive cycle.

7. The kit according to claim 6, wherein the norethindrone acetate equivalent amount of progestogen in the Phase I, II and III compositions is about 1 mg of norethindrone acetate.

8. The kit according to claim 7, wherein the ethinyl estradiol equivalent amount of estrogen in the Phase I composition is about 25 mcg ethinyl estradiol, the ethinyl estradiol equivalent amount of estrogen in the Phase II composition is about 30 mcg of ethinyl estradiol, the ethinyl estradiol equivalent amount of estrogen in the Phase III composition is about 25 mcg of ethinyl estradiol, and the Phase IV composition contains about 75 mg of ferrous fumarate.

9. The kit according to claim 8, wherein the estrogen and progestogen in the Phase I, II and III compositions are, respectively, ethinyl estradiol and norethindrone acetate.

10. The kit according to claim 7, wherein the ethinyl estradiol equivalent amount of estrogen in the Phase I composition is about 20 mcg ethinyl estradiol, the ethinyl estradiol equivalent amount of estrogen in the Phase II composition is about 25 mcg of ethinyl estradiol, the ethinyl estradiol equivalent amount of estrogen in the Phase III composition is about 20 mcg of ethinyl estradiol, and the Phase IV composition contains about 75 mg of ferrous fumarate.

11. The kit according to claim 10, wherein the estrogen and progestogen in the Phase I, II and III compositions are, respectively, ethinyl estradiol and norethindrone acetate.

12. The kit according to claim 1, wherein the kit contains a plurality of groups of dosages of Phase I, II, and III compositions, wherein each group of dosages of Phase I composition contains about 4 to about 7 dosages, each group of dosages of Phase II compositions contains about 8 to about 16 dosages and each group of dosages of Phase III compositions contains about 4 to about 7 dosages.

13. The kit according to claim 12, wherein the number of groups of dosages of Phase I, II, and III compositions is from about 2 to about 9.

14. The kit according to claim 13, wherein said kit contains one group of dosages of a Phase IV composition that amounts to about 2 to about 9 daily dosages.

15. The kit according to claim 14, wherein the norethindrone acetate equivalent amount of progestogen in the Phase I, II, and III compositions is about 1 mg of norethindrone acetate.

16. The kit according to claim 15, wherein the ethinyl estradiol equivalent amount of estrogen in the Phase I composition is about 20 mcg of ethinyl estradiol, the ethinyl estradiol equivalent amount of estrogen in the Phase II composition is about 25 mcg of ethinyl estradiol, and the ethinyl estradiol equivalent amount of estrogen in the Phase III composition is about 20 mcg of ethinyl estradiol.

17. The kit according to claim 16, wherein the estrogen and progestogen in the Phase I, II and III compositions are, respectively, ethinyl estradiol and norethindrone acetate.

18. The kit according to claim 17, wherein each group of dosages of the Phase I composition contains about 5 dosages, each group of dosages of the Phase II composition contains about 11 to about 14 dosages, and each group of dosages of the Phase III composition contains about 5 dosages.

19. The kit according to claim 15, wherein the ethinyl estradiol equivalent amount of estrogen in the Phase I composition is about 25 mcg of ethinyl estradiol, the ethinyl estradiol equivalent amount of estrogen in the Phase II composition is about 30 mcg of ethinyl estradiol, and the ethinyl estradiol equivalent amount of estrogen in the Phase III composition is about 25 mcg of ethinyl estradiol.

20. The kit according to claim 19, wherein the estrogen and progestogen in the Phase I, II and III compositions are, respectively, ethinyl estradiol and norethindrone acetate.

21. The kit according to claim 20, wherein each group of dosages of the Phase I composition contains about 5 dosages, each group of dosages of the Phase II composition contains about 11 to about 14 dosages, and each group of dosages of the Phase III composition contains about 5 dosages.

\* \* \* \* \*